(12) United States Patent
Martin

(10) Patent No.: US 11,166,729 B2
(45) Date of Patent: Nov. 9, 2021

(54) METHOD AND DEVICE FOR SECLUDING A BODY VESSEL

(71) Applicant: Basis Medical, LLC, Atlanta, GA (US)

(72) Inventor: David A. Martin, Atlanta, GA (US)

(73) Assignee: Basis Medical, LLC, Atlanta, GA (US)

( * ) Notice: Subject to any disclaimer, the term of this patent is extended or adjusted under 35 U.S.C. 154(b) by 364 days.

(21) Appl. No.: 14/978,021

(22) Filed: Dec. 22, 2015

(65) Prior Publication Data

US 2017/0172580 A1 Jun. 22, 2017

(51) Int. Cl.
*A61B 17/12* (2006.01)
*A61M 39/24* (2006.01)
(Continued)

(52) U.S. Cl.
CPC .. *A61B 17/12045* (2013.01); *A61B 17/12109* (2013.01); *A61B 17/12136* (2013.01);
(Continued)

(58) Field of Classification Search
CPC .......... A61M 2025/1015; A61M 25/10; A61M 25/1011; A61M 25/0125; A61M 25/0075; A61M 2025/1052; A61M 2025/0036; A61M 25/00; A61M 25/007; A61M 25/0032; A61M 25/0029; A61M 25/003; A61M 2025/1061; A61M 2025/1013; A61M 2025/0076; A61M 39/24; A61B 17/12045; A61B 17/12109; A61B 2017/12127; A61B 17/00008; A61B 17/12186; A61B 17/12136; A61B 2017/00778; A61B 2017/1205; A61B 2017/005; A61B 2090/3782; A61B 2090/378; A61B 2090/3788; A61B 2090/3786

See application file for complete search history.

(56) References Cited

U.S. PATENT DOCUMENTS

| 5,022,399 A | 6/1991 | Biegeleisen |
| 5,224,938 A | 7/1993 | Fenton, Jr. |

(Continued)

OTHER PUBLICATIONS

Ninia, Jerry G., "Treatment of Vulvar Varicosities by Injection-Compression Sclerotherapy"; Dermatologic Surgery 1997;23:573-575.

(Continued)

*Primary Examiner* — Amber R Stiles
*Assistant Examiner* — Alexandra Lalonde
(74) *Attorney, Agent, or Firm* — Alston & Bird LLP

(57) ABSTRACT

A device for secluding a body vessel may include a distal balloon, a proximal balloon, an aspiration port positioned adjacent to the distal balloon, an injection port positioned adjacent to the proximal balloon, and a lumen assembly. The lumen assembly may comprise a central lumen, a distal balloon lumen operably coupled to the distal balloon, a proximal balloon lumen operably coupled to the proximal balloon, an aspiration port lumen operably coupled to the aspiration port, and an injection port lumen operably coupled to the injection port. The distal balloon and the proximal balloon may define a treatment chamber therebetween, and the aspiration port and the injection port may be positioned within the treatment chamber on the lumen assembly.

9 Claims, 7 Drawing Sheets

(51) Int. Cl.
*A61B 90/00* (2016.01)
*A61M 25/10* (2013.01)

(52) U.S. Cl.
CPC ....... *A61B 17/12186* (2013.01); *A61M 39/24* (2013.01); *A61B 2090/378* (2016.02); *A61B 2217/005* (2013.01); *A61M 2025/1052* (2013.01)

(56) References Cited

U.S. PATENT DOCUMENTS

| | | | | |
|---|---|---|---|---|
| 5,460,610 | A * | 10/1995 | Don Michael | A61M 25/0133 604/101.03 |
| 5,662,609 | A * | 9/1997 | Slepian | A61L 24/0031 604/101.03 |
| 8,162,879 | B2 | 4/2012 | Hattangadi et al. | |
| 8,603,064 | B2 | 12/2013 | Hattangadi et al. | |
| 2002/0010418 | A1 * | 1/2002 | Lary | A61M 25/10 604/101.04 |
| 2004/0225251 | A1 | 11/2004 | Glickman | |
| 2005/0273050 | A1 * | 12/2005 | Yokoyama | A61M 25/1011 604/101.03 |
| 2006/0095015 | A1 * | 5/2006 | Hobbs | A61B 17/12186 604/508 |
| 2009/0203995 | A1 * | 8/2009 | Matonick | A61M 25/1011 600/435 |
| 2009/0318855 | A1 * | 12/2009 | Ehrenreich | A61M 25/1011 604/28 |
| 2010/0082012 | A1 * | 4/2010 | Hattangadi | A61L 29/16 604/509 |
| 2011/0218494 | A1 * | 9/2011 | Gerrans | A61B 17/320725 604/101.05 |
| 2012/0310269 | A1 | 12/2012 | Fearnot | |
| 2014/0046243 | A1 | 2/2014 | Ray et al. | |
| 2014/0150782 | A1 * | 6/2014 | Vazales | A61M 16/0463 128/202.16 |
| 2014/0163525 | A1 | 6/2014 | Starnberg | |
| 2015/0174379 | A1 * | 6/2015 | Bagaoisan | A61M 25/003 604/509 |
| 2015/0190127 | A1 * | 7/2015 | Madsen | A61B 17/00491 606/201 |
| 2015/0209560 | A1 * | 7/2015 | Teeslink | A61B 17/12045 604/509 |
| 2015/0343136 | A1 | 12/2015 | Nitzan et al. | |
| 2017/0232238 | A1 | 8/2017 | Biller et al. | |

OTHER PUBLICATIONS

International Search Report and Written Opinion for corresponding International Application No. PCT/US2016/033510, dated Aug. 5, 2016.

Office Action for Canadian Application No. 2,986,475 dated Sep. 24, 2018, 4 pages.

\* cited by examiner

METHOD AND DEVICE FOR SECLUDING A BODY VESSEL

FIELD OF THE INVENTION

The following invention generally relates to the field of body vessel seclusion.

BACKGROUND OF THE INVENTION

For certain medical conditions, it may be necessary or desirable to seclude (i.e., to close off, collapse, or significantly narrow) a body vessel such as a vein or artery. One situation in which seclusion may be desirable is in the treatment of varicose veins, which are swollen, twisted, or enlarged veins that may be visible under a patient's skin. By closing off the varicose vein, blood ceases to flow in the varicose vein and is naturally redirected to healthy veins. Over time, the closed-off vein may be completely absorbed into surrounding tissue.

There are several techniques currently in use for secluding a blood vessel such as a varicose vein. Examples of these techniques include surgery, heat ablation, and chemical treatment. Surgically, veins may be subjected to a seclusion procedure known as ligation. During ligation, a small incision may be made near the target vein and the vein may be tied off. The ligated vein may be left in place and absorbed into surrounding tissue, as noted above. Alternatively, the ligated vein may be removed by a process known as "stripping" the vein. The surgical treatment of veins in this manner is sometimes referred to as phlebectomy.

The surgical treatment of varicose veins is generally effective, but may carry certain risks and disadvantages. The procedure is relatively invasive compared to other varicose vein treatment methods, and accordingly may be painful for some patients. Surgical treatment of varicose veins also carries a risk of nerve injury, may require the use of general anesthesia and an overnight hospital stay, and may require a relatively long recovery time. Accordingly, other types of vein treatment have been developed. These treatments generally involve damaging the walls of the vein, which causes the vein walls to collapse, close, or narrow. For example, in heat ablation treatment, a heat source (typically a laser or radio frequency transmitter) may be inserted into the vein through a catheter. Upon reaching a target area of the vein, the heat source may be turned on for a predetermined period of time, which damages the target area of the vein and causes scar tissue to form on the inner walls of the vein. The build-up of scar tissue closes the vein. Problematically, the same heat that damages the vein can also damage surrounding tissue and nearby nerves. It can also cause skin burns and blood clots, and may not be appropriate for all types of veins.

The vein walls can also be damaged chemically in a procedure known as sclerotherapy. In sclerotherapy, a chemical known as a sclerosing agent may be injected into the vein. The sclerosing agent may damage the walls of the vein and cause the vein to narrow or close. However, in order to be effective, the sclerosing agent needs to remain in contact with the inside walls of the target area of the vein for some time (e.g., up to one minute). This is difficult to achieve using conventional sclerotherapy procedures because the sclerosing agent may be quickly washed away by the flow of blood through the vein. As a result, the sclerosing agent may be diluted and flow to other portions of the body, and hence the sclerosing agent may not be sufficiently effective to close the vein upon an initial application. Accordingly, patients may need several treatment sessions with one or more injections of sclerosing agent applied in each session. In order to address these issues, a new sclerotherapy treatment method called catheter-directed foam sclerotherapy ("CDFS") has recently been employed. In this method, a catheter is inserted into the vein and moved to the target site. The sclerosing agent is injected into the vein through the catheter in the form of a foam. Because the agent is a foam, it is relatively more difficult for the blood flow to dilute and remove the sclerosing agent. Therefore, as compared to conventional sclerotherapy, CDFS allows the sclerosing agent to be present at the target site for a relatively longer period of time, in a relatively larger concentration. Nonetheless, the sclerosing agent will still be washed away from the target site due to the flow of the blood in the vein, so repeated treatments may remain necessary.

Therefore there at least remains a need in the art for a method and device for secluding a body vessel such that a sclerosing agent may be maintained at the target site without being washed away due to blood flow in the vessel.

SUMMARY OF THE INVENTION

One or more embodiments of the invention may address one or more of the aforementioned problems. In one aspect, a device for secluding a body vessel is provided. In accordance with certain embodiments, the device may include a distal balloon, a proximal balloon, an aspiration port positioned adjacent to the distal balloon, an injection port positioned adjacent to the proximal balloon, and a lumen assembly. The lumen assembly may comprise a central lumen, a distal balloon lumen operably coupled to the distal balloon, a proximal balloon lumen operably coupled to the proximal balloon, an aspiration port lumen operably coupled to the aspiration port, and an injection port lumen operably coupled to the injection port. The distal balloon and the proximal balloon may define a treatment chamber therebetween, and the aspiration port and the injection port may be positioned within the treatment chamber on the lumen assembly.

In another aspect, a method for secluding a body vessel is provided. In accordance with certain embodiments, the method may include removing blood from a treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port. The aspiration port may be operably coupled to an aspiration port lumen of a vessel seclusion device, and the injection port may be operably coupled to an injection port lumen of the vessel seclusion device.

In yet another aspect, another method for secluding a body vessel is provided. In accordance with certain embodiments, the method may include selecting a seclusion length of the body vessel such that the seclusion length has a starting point and an ending point, dividing the seclusion length into at least two treatment chambers, secluding the first treatment chamber with a vessel seclusion device, moving the vessel seclusion device to the second treatment chamber, and secluding the second treatment chamber. The first treatment chamber may be defined by the starting point and a first intermediate point, and the second treatment chamber may be defined by the first intermediate point and the ending point. Secluding each of the first treatment chamber and the second treatment chamber may comprise removing blood from the treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port. The aspiration port may be operably coupled to an aspiration port lumen of a vessel seclusion device, and the injection port may be operably coupled to an injection port lumen of the vessel seclusion device.

BRIEF DESCRIPTION OF THE DRAWINGS

Exemplary embodiments now will be described more fully hereinafter with reference to the accompanying drawings, in which some, but not all embodiments of the invention are shown. The present invention may be embodied in many different forms and should not be construed as limited to the embodiments set forth herein; rather, these embodiments are provided so that this disclosure will satisfy applicable legal requirements and demonstrate exemplary embodiments of the invention. Repeat use of reference characters in the present specification and drawings is intended to represent same or analogous features or elements of the invention.

DETAILED DESCRIPTION OF EXEMPLARY EMBODIMENTS

Figure 1:
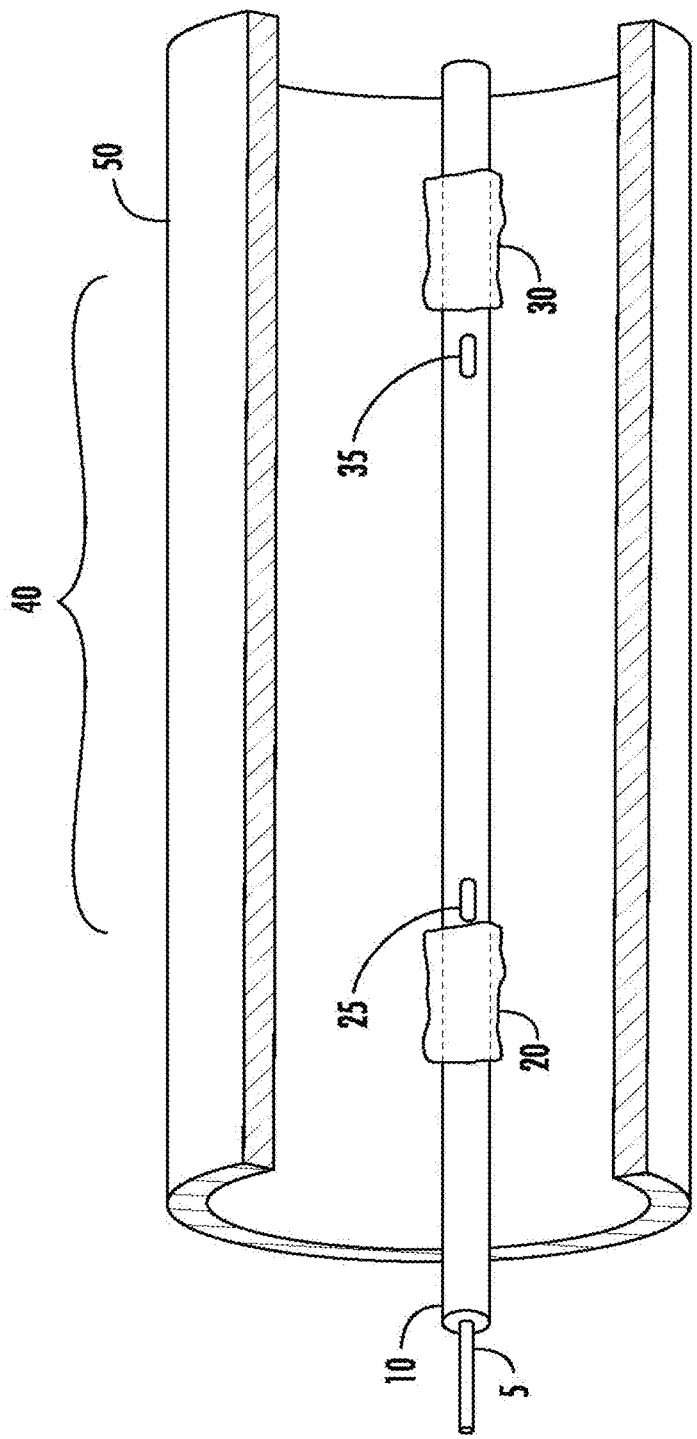
FIG. 1 illustrates a partial view of a device for secluding a body vessel in a pre-deployed form according to an example embodiment.

Reference will now be made in detail to exemplary embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

In contrast to conventional treatment methods and devices, the exemplary embodiments disclosed herein may be less invasive and may require less recovery time. Moreover, the exemplary embodiments disclosed herein may eliminate the need for a general anesthetic, instead relying on a local anesthetic. In this regard, the exemplary embodiments disclosed herein may reduce procedural risks and further decrease required recovery time. In addition, the exemplary embodiments disclosed herein may be associated with a reduced risk of nerve damage, skin damage, and recovery pain.

As used herein, the term "body vessel" may comprise any lumen or other similar region in a body, such as a blood vessel or the intestines. Although specific examples are provided herein with reference to veins, one of ordinary skill in the art will recognize that the device and methods disclosed herein are not limited to these particular examples but rather may be employed in any suitable body vessel.

The term "seclusion", as used herein, may refer to the narrowing, collapsing, or closing off of a body vessel. Accordingly, seclusion may be distinct from therapies intended to open or widen a vessel and from therapies intended to prevent the vessel from narrowing. The term "two-point seclusion", as used herein, may refer to secluding the body vessel at two points with a narrowed, collapsed, or closed space between the points.

For ease of reference, exemplary embodiments will be described in terms of use in human subjects. It will be understood, however, that such descriptions are not limited to use to humans, but will also include use in other animals unless explicitly stated otherwise. Moreover, although a catheter is referred to herein, one of ordinary skill in the art will recognize that a catheter is merely an exemplary device as disclosed herein.

In one aspect, a device for secluding a body vessel is provided. In accordance with certain embodiments, the device for secluding a body vessel may include a distal balloon, a proximal balloon, an aspiration port positioned adjacent to the distal balloon, an injection port positioned adjacent to the proximal balloon, and a lumen assembly. In some embodiments, for instance, the lumen assembly may comprise a central lumen, a distal balloon lumen operably coupled to the distal balloon, a proximal balloon lumen operably coupled to the proximal balloon, an aspiration port lumen operably coupled to the aspiration port, and an injection port lumen operably coupled to the injection port. In certain embodiments, for example, the distal balloon and the proximal balloon may define a treatment chamber therebetween, and the aspiration port and the injection port may be positioned within the treatment chamber on the lumen assembly.

FIG. 1, for instance, illustrates a partial view of a device for secluding a body vessel in a pre-deployed form according to an example embodiment. As shown in FIG. 1, for example, the device may be a catheter. The catheter may include a lumen assembly 10, a proximal balloon 20, an injection port 25 positioned adjacent to the proximal balloon 20, a distal balloon 30, and an aspiration port 35 positioned adjacent to the distal balloon 30. The proximal balloon 20 and the distal balloon 30 may define a treatment chamber 40 therebetween inside of a body vessel 50 when the balloons 20, 30 are inflated. In this regard, for example, a chemical agent may be introduced into the treatment chamber 40 to seclude the body vessel 50 within the treatment chamber 40. The balloons 20, 30 may be made of any suitable material as understood by one of ordinary skill in the art including, but not limited to, polymeric materials. In accordance with certain embodiments, for example, the body vessel 50 may comprise at least one of a varicose vein, a portal vein, a perforator vein, a superficial vein, a peripheral vein, an arteriovenous malformation, or any combination thereof. The catheter may be of any length suitable for secluding a variety of body vessels as understood by one of ordinary skill in the art (e.g., 100 cm).

According to certain embodiments, for instance, the treatment chamber 40 may comprise a length from about 3 cm to about 15 cm. In some embodiments, for example, the treatment chamber 40 may comprise a length from about 5 cm to about 10 cm. In further embodiments, for instance, the treatment chamber 40 may comprise a length from about 6 cm to about 8 cm. In certain embodiments, for example, the treatment chamber 40 may comprise a length of about 7 cm. As such, in certain embodiments, the treatment chamber 40 may comprise a length from at least about any of the following: 3, 4, 5, 6, and 7 cm and/or at most about 15, 12, 10, 9, 8, and 7 cm (e.g., about 4-9 cm, about 6-12 cm, etc.).

The lumen assembly 10 may comprise a flexible tube having several hollow lumens therein as described in more detail below. The individual lumens may not be very flexible. For example, the individual lumens within the lumen assembly 10 may only bend and/or move from about 2 mm to about 3 mm. However, the lumen assembly 10 may be sufficiently flexible to navigate through the body vessels of an individual. For instance, the lumen assembly 10 may be used to guide the device into position inside the body vessel 50, for example, via a guide wire 5.

According to certain embodiments, for instance, the guide wire 5 may comprise a diameter from about 0.001 cm to about 0.025 cm. In some embodiments, for example, the guide wire 5 may comprise a diameter from about 0.01 cm to about 0.02 cm. In further embodiments, for instance, the guide wire 5 may comprise a diameter from about 0.015 cm to about 0.019 cm. In other embodiments, for example, the guide wire 5 may comprise a diameter of about 0.018 cm. As such, in certain embodiments, the guide wire 5 may comprise a diameter from at least about any of the following: 0.001, 0.005, 0.01, 0.015, 0.016, 0.017, and 0.018 cm and/or at most about 0.025, 0.024, 0.023, 0.022, 0.021, 0.02, 0.019, and 0.018 cm (e.g., about 0.01-0.019 cm, about 0.017-0.024 cm, etc.). However, the guide wire 5 may comprise any guide wire suitable for use with the device disclosed herein as understood by one of ordinary skill in the art.

In accordance with certain embodiments, for instance, the lumen assembly 10 may include the injection port 25 and the aspiration port 35 to introduce and evacuate fluids respectively. In certain embodiments, for example, the injection port 25 and the aspiration port 35 may be positioned on the lumen assembly 10 within the treatment chamber 40 created by the inflated proximal balloon 20 and the distal balloon 30. In some embodiments, for example, each of the aspiration port 35 and the injection port 25 comprise a port orifice and a one-way valve at the port orifice. In this regard, for instance, the aspiration port 35 may evacuate blood and other bodily fluids from the treatment chamber 40 to provide an empty area for the chemical agent to occupy and to prevent the chemical agent from being diluted. Additionally, the aspiration port 35 may evacuate the chemical agent from the treatment chamber 40 after treatment. Moreover, the injection port 25 may introduce the chemical agent into the treatment chamber 40 to initiate seclusion of the body vessel 50.

Figure 2:
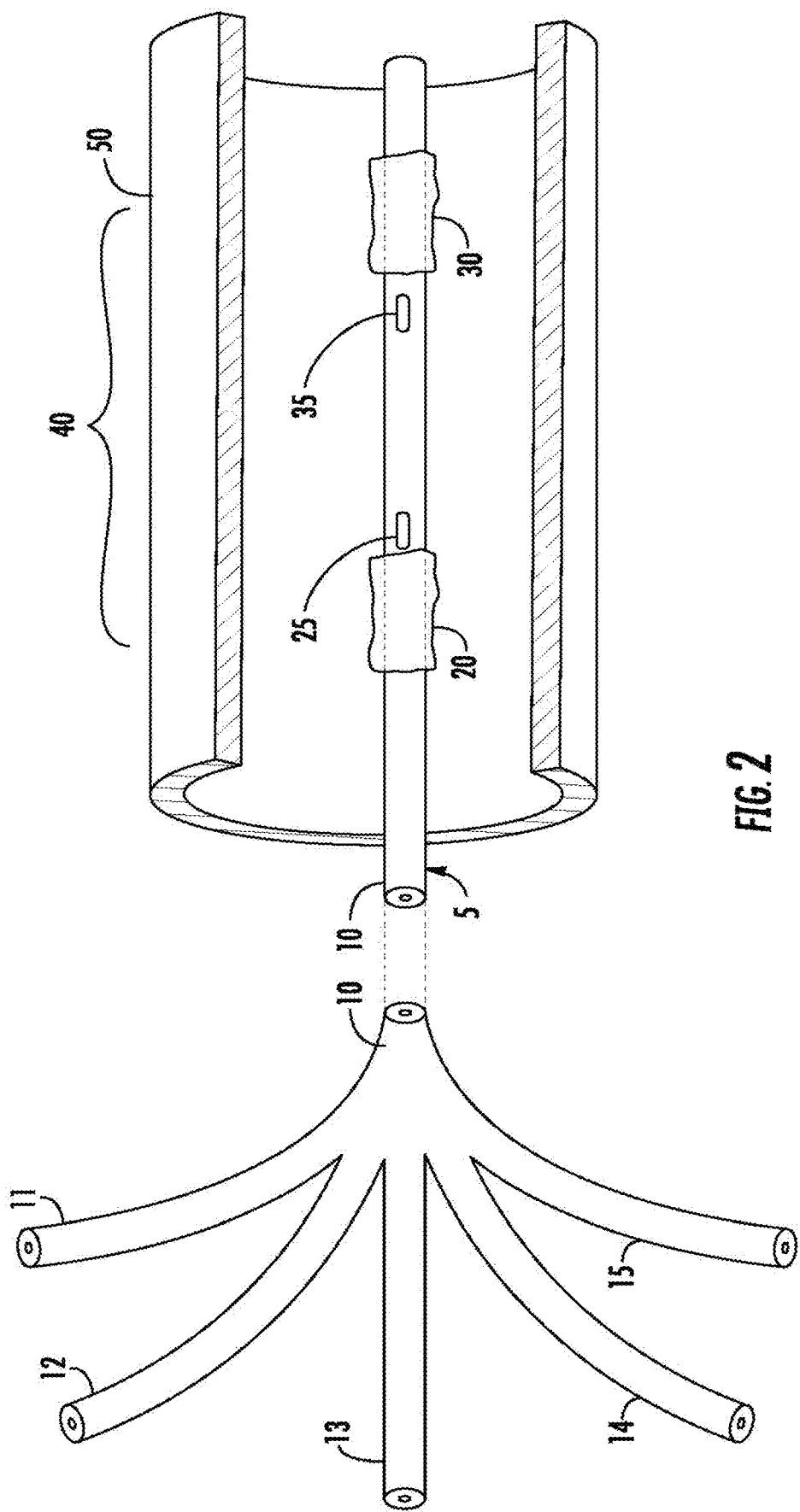
FIG. 2 illustrates a device for secluding a body vessel including the lumens according to an example embodiment.
Figure 3:
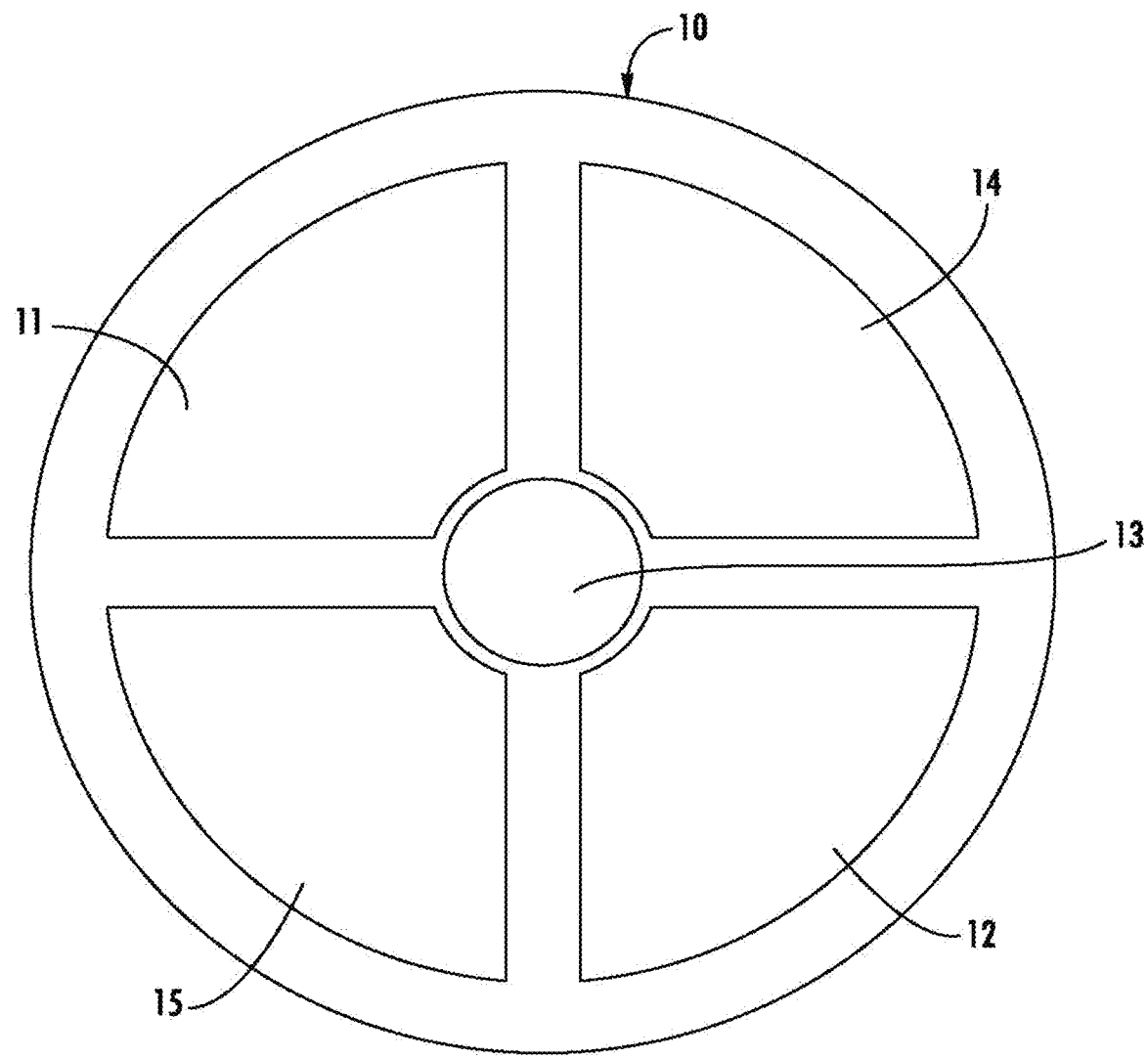
FIG. 3 illustrates a cross-section of a lumen assembly in a device for secluding a body vessel according to an example embodiment.

FIG. 2, for instance, illustrates a device for secluding a body vessel including the lumens according to an example embodiment. As shown in FIG. 2, for example, the lumen assembly 10 divides into individual lumens outside of the body vessel 50. The individual lumens include a distal balloon lumen 11, a proximal balloon lumen 12, a central lumen 13, an injection port lumen 14, and an aspiration port lumen 15. FIG. 3, for instance, illustrates a cross-section of the lumen assembly 10 in a device for secluding a body vessel according to an example embodiment. As shown in FIG. 3, for example, the lumen assembly 10 channels each of the lumens 11-15 through a single tube such that the distal balloon lumen 11, the proximal balloon lumen 12, the injection port lumen 14, and the aspiration port lumen 15 are arranged around the central lumen 13 such that the two balloon lumens 11, 12 are positioned diagonally across from each other within the lumen assembly 10. The two port lumens 14, 15 are similarly positioned diagonally across from each other within the lumen assembly 10.

According to certain embodiments, for example, the central lumen 13 is configured to introduce the guide wire 5 into the body vessel 50. Prior to the guide wire 5 moving through the central lumen 13, the body vessel 50 may be prepared. For example, an incision in a patient's skin may be made, and the body vessel 50 may be opened at the location of the incision. The guide wire 5 may then be inserted into the opening in the body vessel 50 and threaded through the body vessel 50 under guidance of a visualization device (e.g., ultrasound 95), as described in more detail below. When the guide wire 5 reaches the appropriate treatment point within the body vessel 50, the central lumen 13 may be threaded over the guide wire 5 and into the body vessel 50. The central lumen 13 (and similarly the entire device) may be pushed along the length of the guide wire 5 until the distal balloon 30 is in a suitable location in the body vessel 50 as indicated by the visualization device.

According to certain embodiments, for instance, the aspiration port 35 and the aspiration port lumen 15 may be configured to remove at least one of blood, bodily fluid, a chemical agent, or any combination thereof from the treatment chamber 40. In further embodiments, for example, the injection port 25 and the injection port lumen 14 may be configured to deliver a chemical agent to the treatment chamber 40.

Moreover, according to certain embodiments, for instance, the proximal balloon 20 and the distal balloon 30 may be inflated through the proximal balloon lumen 12 and the distal balloon lumen 11 respectively. The balloons 20, 30 may be inflated using air or any other suitable fluid as understood by one of ordinary skill in the art. In this regard, the inflation of the balloons 20, 30 may secure the catheter in place and isolate the treatment chamber 40.

Figure 4:
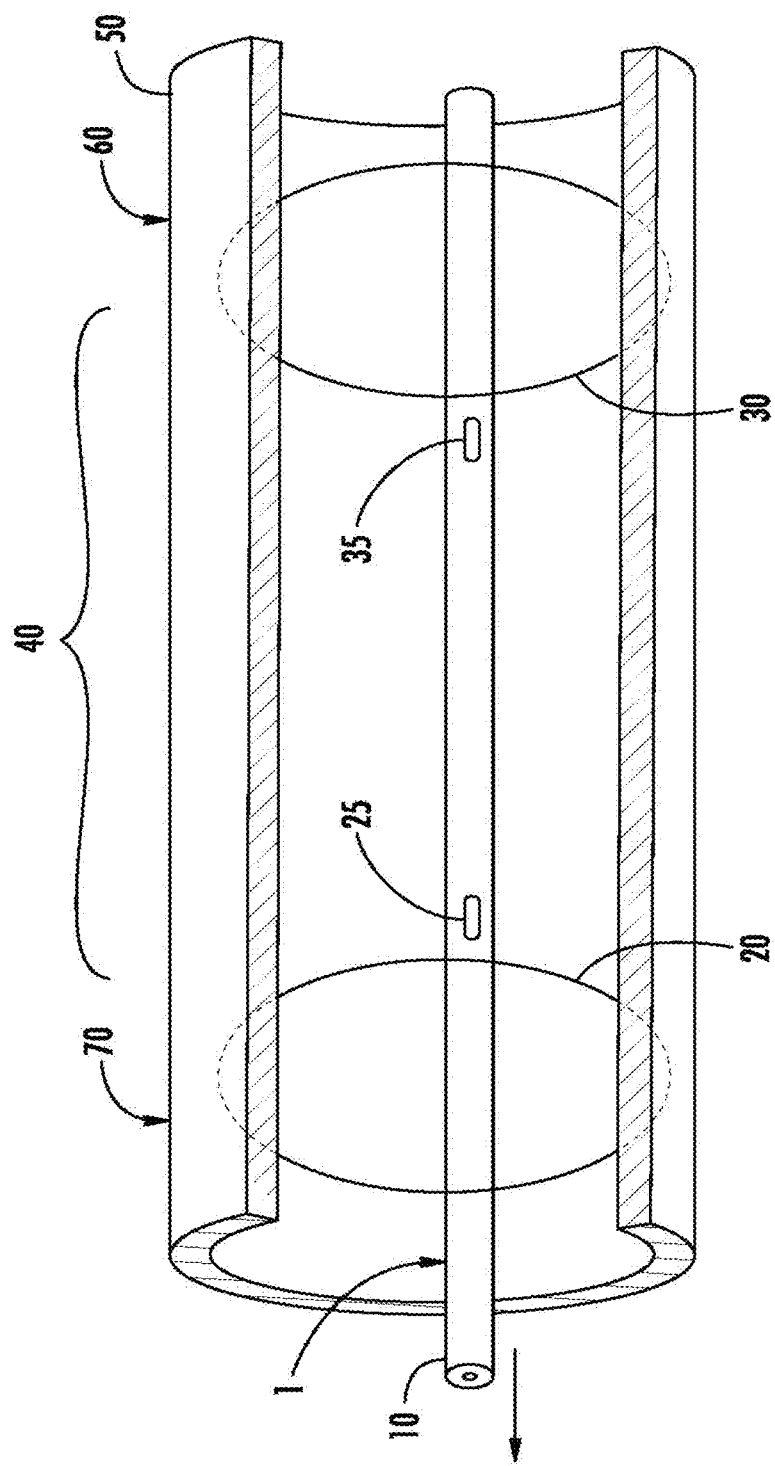
FIG. 4 illustrates a partial view of a device for secluding a body vessel in a deployed form according to an example embodiment.

FIG. 4, for example, illustrates a partial view of a device for secluding a body vessel in a deployed form according to an example embodiment. As shown in FIG. 4, for instance, the balloons 20, 30 are inflated to define the treatment chamber 40. To define the treatment chamber 40, for example, the proximal balloon 20 and the distal balloon 30 may be inflated with a fluid. When inflated, for instance, the interior sides of the distal balloon 30 and the proximal balloon 20 (i.e. the sides facing internally towards each other) may define the outer limits (e.g., starting point 60 and ending point 70) of the treatment chamber 40. For example, the proximal and distal balloons 20, 30 may be sized so that, when inflated, the outer ends of the balloons 20, 30 contact the interior surface of the body vessel 50 and form a seal, preventing fluids from entering or leaving the treatment chamber 40. According to certain embodiments, each of the distal balloon 30 and the proximal balloon 20 are spherical. However, the balloons 20, 30 may be any shape suitable for use in the device as understood by one of ordinary skill in the art.

In some embodiments, for instance, the distal balloon 30 may comprise an inflated distal balloon diameter, the proximal balloon 20 may comprise an inflated proximal balloon diameter, and each of the inflated distal balloon diameter and the inflated proximal balloon diameter may be from about 5 mm to about 20 mm. In further embodiments, for example, each of the inflated distal balloon diameter and the inflated proximal balloon diameter may be from about 7 mm to about 15 mm. In other embodiments, for instance, each of the inflated distal balloon diameter and the inflated proximal balloon diameter may be from about 8 mm to about 12 mm. As such, in certain embodiments, each of the inflated distal balloon diameter and the inflated proximal balloon diameter may be from at least about any of the following: 5, 6, 7, and 8 mm and/or at most about 20, 19, 18, 17, 16, 15, 14, 13, and 12 mm (e.g., about 6-18 mm, about 5-14 mm, etc.).

In another aspect, a method for secluding a body vessel is provided. In accordance with certain embodiments, the method may include removing blood from a treatment chamber 40 in the body vessel 50 via an aspiration port 35, delivering a chemical agent to the treatment chamber 40 via an injection port 25, maintaining the chemical agent in the treatment chamber 40 for a predetermined period of time to seclude the body vessel 50 within the treatment chamber 40, and removing the chemical agent from the treatment chamber 40 via the aspiration port 35. The aspiration port 35 may be operably coupled to an aspiration port lumen 15 of a vessel seclusion device (e.g., catheter), and the injection port 25 may be operably coupled to an injection port lumen 14 of the vessel seclusion device.

Figure 6:
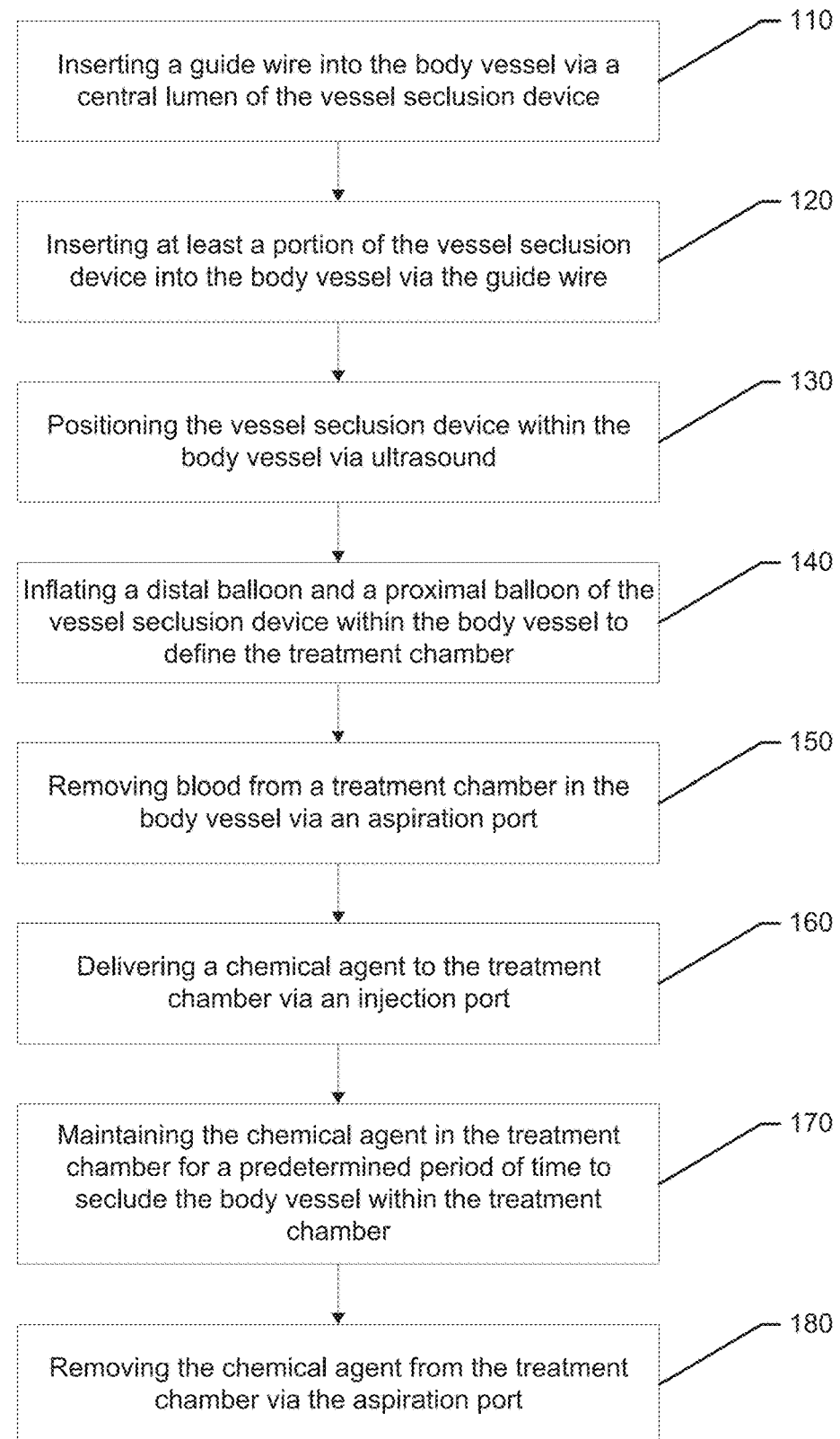
FIG. 6 illustrates a block diagram of a method of secluding a body vessel according to an example embodiment.

FIG. 6, for example, illustrates a block diagram of a method of secluding a body vessel 50 according to an example embodiment. As shown in FIG. 6, for instance, the method includes the initial steps of inserting a guide wire 5 into the body vessel 50 via a central lumen 13 of the vessel seclusion device at operation 110, inserting at least a portion of the vessel seclusion device into the body vessel 50 via the guide wire 5 at operation 120, positioning the vessel seclusion device within the body vessel 50 via ultrasound 95 at operation 130, and inflating a distal balloon 30 and a proximal balloon 20 of the vessel seclusion device within the body vessel 50 to define the treatment chamber 40 at operation 140. The method continues with the primary treatment steps of removing blood from the treatment chamber 40 in the body vessel 50 via an aspiration port 35 at operation 150, delivering a chemical agent to the treatment chamber 40 via an injection port 25 at operation 160, maintaining the chemical agent in the treatment chamber 40 for a predetermined period of time to seclude the body vessel 50 within the treatment chamber 40 at operation 170, and removing the chemical agent from the treatment chamber 40 via the aspiration port 35 at operation 180.

In accordance with certain embodiments, for instance, the chemical agent may be any agent known to chemically damage the body vessel 50 into which the catheter has been introduced, thereby causing the body vessel 50 to narrow or close. In some embodiments, for example, the chemical agent may be a sclerosing agent typically used in sclerotherapy including, but not limited to, polidocanol, sotradecol, hypertonic saline, or any other chemical agent suitable for damaging the vessel in the context of the sclerosing effect as understood by one of ordinary skill in the art. Alternatively or in addition, for instance, the chemical agent may be an agent known to elicit a biological response from the body vessel 50 into which the catheter has been introduced. In such embodiments, for example, the agent may be selected so as to induce the biological reaction substantially immediately after the catheter is withdrawn from the treatment chamber 40 (i.e. the body vessel 50 closes or narrows around the catheter as the catheter is withdrawn from the body vessel 50). In this regard, the body vessel 50 may be caused to immediately close following application of the chemical agent (as compared to traditional sclerotherapies, in which the vessel may take several days, or even several weeks, to close following application of the sclerosing agent).

According to certain embodiments, for example, after evacuating the treatment chamber 40 of all blood and/or other bodily fluids via the aspiration port lumen 15 and the aspiration port 35, a chemical agent may be introduced into the treatment chamber 40 via the injection port lumen 14 and injection port 25 and then maintained in the treatment chamber 40 for a predetermined amount of time due to the inflated balloons 20, 30. In some embodiments, for instance, maintaining the chemical agent in the treatment chamber for the predetermined period of time may comprise maintaining the chemical agent in the treatment chamber for up to one minute (i.e. from about 1 second to about 60 seconds). As such, in certain embodiments, for instance, the chemical agent may be maintained in the treatment chamber for a time from at least about any of the following: 1, 5, 10, 20, 30, 40, 50, and 60 seconds and/or at most 60 seconds (e.g., about 5-60 seconds, about 30-60 seconds, etc.). In this regard, the chemical agent remains in contact with walls of the body vessel 50 in the treatment chamber 40 for a sufficient amount of time to seclude the body vessel 50 without being diluted or washed away by the flow of fluid in the body vessel 50 shortly after introduction of the chemical agent. After the predetermined period of time, the chemical agent may be removed from the body vessel 50 via the aspiration port 35 and the aspiration port lumen 15. If the treatment chamber 40 fully encompassed the area to be secluded, the balloons 20, 30 may be deflated and the catheter may be withdrawn from the body vessel 50 through the original incision. The original incision in the body vessel 50 and/or skin may then be closed (e.g., via sutures). In this regard, the body vessel 50 may be secluded between two points (e.g., the starting point 60 and the ending point 70 in FIG. 4).

Following treatment, a patient will typically be capable of walking immediately and can return home after the procedure (i.e. the patient does not need to remain in a hospital overnight). The body vessel 50 may be secluded immediately, as opposed to conventional sclerotherapy, which may require additional time following treatment and/or multiple treatments in order to seclude the body vessel 50, and the body vessel 50 may be absorbed into surrounding tissue over a period of several months. The patient may be scheduled for a follow-up visit to verify that the body vessel 50 has been properly secluded and absorbed. If a problem is noted at the follow-up visit, for instance, the patient may undergo another round of treatment using the methods and devices disclosed herein or may be treated using a different method. In this regard, the methods disclosed herein may be used in combination with other conventional treatments.

In yet another aspect, another method for secluding a body vessel is provided. In accordance with certain embodiments, the method may include selecting a seclusion length of the body vessel such that the seclusion length has a starting point and an ending point, dividing the seclusion length into at least two treatment chambers, secluding the first treatment chamber with a vessel seclusion device (e.g., catheter), moving the vessel seclusion device to the second treatment chamber, and secluding the second treatment chamber. The first treatment chamber may be defined by the starting point and a first intermediate point, and the second treatment chamber may be defined by the first intermediate point and the ending point. Secluding each of the first treatment chamber and the second treatment chamber may comprise removing blood from the treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port as previously discussed herein. The aspiration port may be operably coupled to an aspiration port lumen of a vessel seclusion device, and the injection port may be operably coupled to an injection port lumen of the vessel seclusion device.

Figure 7:
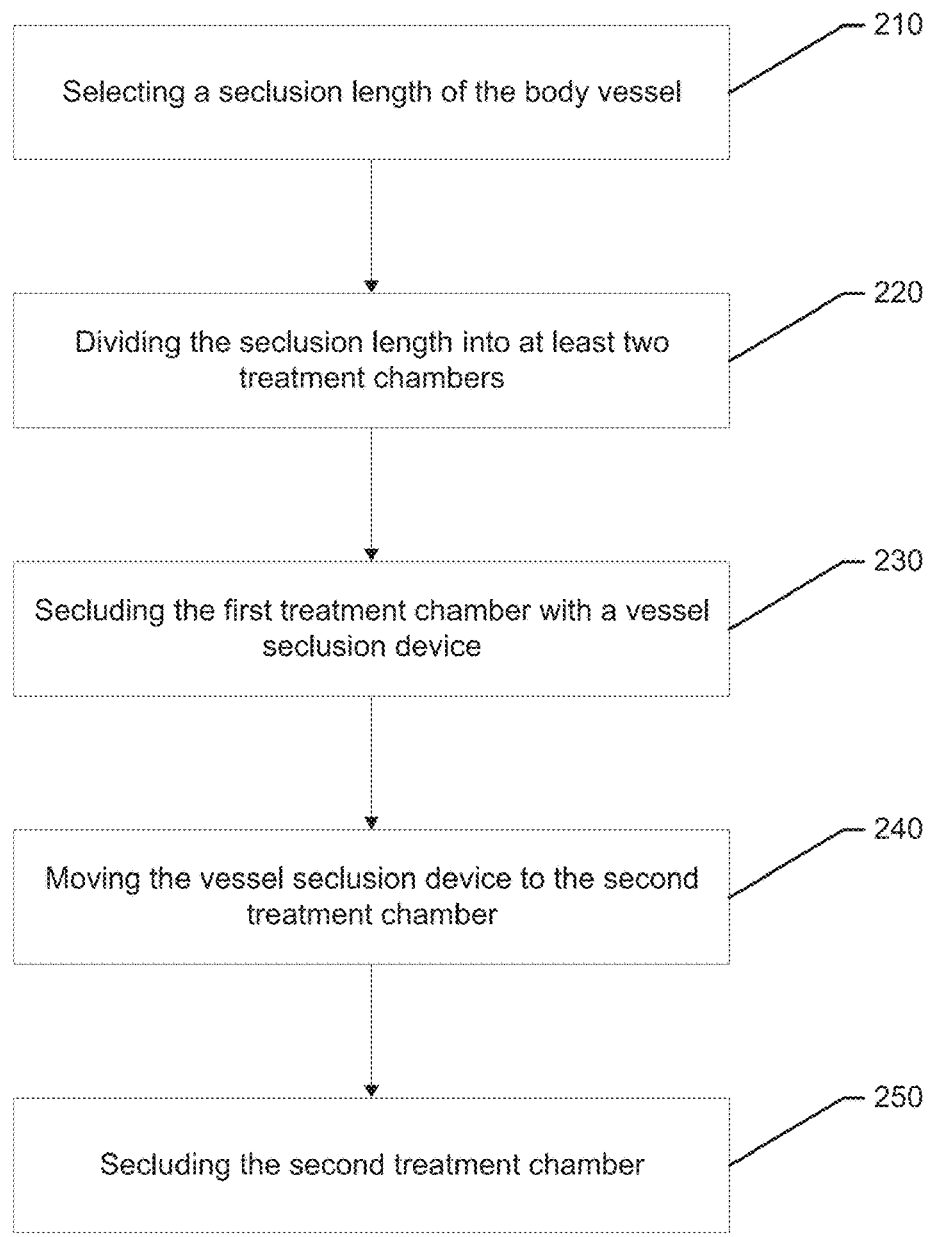
FIG. 7 illustrates a block diagram of a method of secluding a body vessel according to an example embodiment.

FIG. 7, for example, illustrates a block diagram of a method of secluding a body vessel according to an example embodiment. As shown in FIG. 7, for instance, the method includes selecting a seclusion length of the body vessel at operation 210, dividing the seclusion length into at least two treatment chambers at operation 220, secluding the first treatment chamber with a vessel seclusion device at operation 230, moving the vessel seclusion device to the second treatment chamber at operation 240, and secluding the second treatment chamber at operation 250. In this regard, if the seclusion length 100 extends beyond one treatment chamber 40, the catheter may be partially withdrawn in order to reposition the treatment chamber 40 at a new location along the seclusion length 100.

According to certain embodiments, for instance, the seclusion length 100 may be from about 3 cm to about 100 cm. In other embodiments, for example, the seclusion length 100 may be from about 7 cm to about 90 cm. In further embodiments, for instance, the seclusion length 100 may be from about 15 cm to about 80 cm. In some embodiments, for example, the seclusion length 100 may be from about 60 cm to about 70 cm. As such, in certain embodiments, the seclusion length 100 may be from at least about any of the following: 3, 5, 7, 10, 15, 20, 30, 40, 50, and 60 cm and/or at most about 100, 95, 90, 85, 80, 75, and 70 cm (e.g., about 5-70 cm, about 50-60 cm, etc.).

Figure 5:
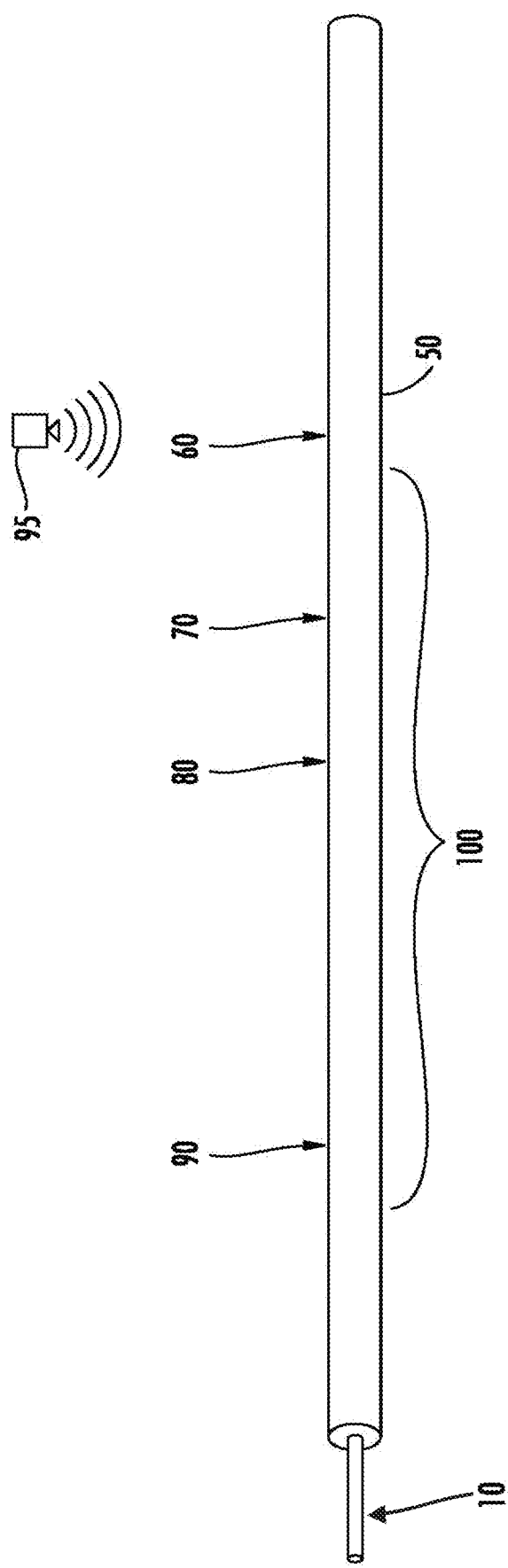
FIG. 5 illustrates a body vessel with an identified area to be secluded according to an example embodiment.

In accordance with certain embodiments, for example, the seclusion length may comprise at least three treatment chambers. In such embodiments, for instance, the first treatment chamber may be defined by the starting point and the first intermediate point, the second treatment chamber may be defined by the first intermediate point and a second intermediate point, and a third treatment chamber may be defined by the second intermediate point and the ending point. FIG. 5, for instance, illustrates a body vessel with an identified area to be secluded according to an example embodiment. As shown in FIG. 5, for example, the seclusion length 100 is divided into three treatment chambers, with the first treatment chamber to be located between the starting point 60 and the first intermediate point 70, the second treatment chamber to be located between the first intermediate point 70 and the second intermediate point 80, and the third treatment chamber to be located between the second intermediate point 80 and the ending point 90.

According to certain embodiments, moving the vessel seclusion device comprises positioning the vessel seclusion device within the body vessel 50 via ultrasound 95. Ultrasound 95 may be used to position the vessel seclusion device because it is not invasive and does not require special equipment to be deployed on the catheter or guide wire 5.

In this regard, the catheter may initially be positioned such that the treatment chamber 40 lies between the starting point 60 and the first intermediate point 70. Following application of the chemical agent between these points 60, 70, the catheter may be repositioned so that the distal balloon 30 is positioned at the first intermediate point 70 and the proximal balloon 20 is positioned at the second intermediate point 80. The method may be repeated until the full seclusion length 100 has been treated such that the proximal balloon 20 is positioned at the ending point 90.

EXEMPLARY EMBODIMENTS

Certain exemplary embodiments provide a device for secluding a body vessel. For instance, this device provides a less invasive, less damaging means for secluding body vessels having a reduced recovery time and that is less likely to require multiple applications. In one aspect, the device for secluding a body vessel includes a distal balloon, a proximal balloon, an aspiration port positioned adjacent to the distal balloon, an injection port positioned adjacent to the proximal balloon, and a lumen assembly. According to certain embodiments, the lumen assembly comprises a central lumen, a distal balloon lumen operably coupled to the distal balloon, a proximal balloon lumen operably coupled to the proximal balloon, an aspiration port lumen operably coupled to the aspiration port, and an injection port lumen operably coupled to the injection port. In some embodiments, the distal balloon and the proximal balloon define a treatment chamber therebetween, and the aspiration port and the injection port are positioned within the treatment chamber on the lumen assembly. In certain embodiments, the treatment chamber comprises a length from about 3 cm to about 15 cm. In further embodiments, the central lumen is configured to introduce a guide wire into the body vessel.

In accordance with certain embodiments, each of the aspiration port and the injection port comprise a port orifice and a one-way valve at the port orifice. In some embodiments, the aspiration port and the aspiration port lumen are configured to remove at least one of blood, bodily fluid, a chemical agent, or any combination thereof from the treatment chamber. In further embodiments, the injection port and the injection port lumen are configured to deliver a chemical agent to the treatment chamber.

According to certain embodiments, each of the distal balloon and the proximal balloon are spherical. In some embodiments, the distal balloon comprises an inflated distal balloon diameter, the proximal balloon comprises an inflated proximal balloon diameter, and each of the inflated distal balloon diameter and the inflated proximal balloon diameter is from about 5 mm to about 20 mm.

In another aspect, certain embodiments provide a method for secluding a body vessel. According to certain embodiments, the method includes removing blood from a treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port. In such embodiments, the aspiration port is operably coupled to an aspiration port lumen of a vessel seclusion device, and the injection port is operably coupled to an injection port lumen of the vessel seclusion device. In some embodiments, the body vessel comprises at least one of a varicose vein, a portal vein, a perforator vein, a superficial vein, a peripheral vein, an arteriovenous malformation, or any combination thereof.

In accordance with certain embodiments, maintaining the chemical agent in the treatment chamber for the predetermined period of time comprises maintaining the chemical agent in the treatment chamber from about 1 second to about 60 seconds. In some embodiments, the chemical agent comprises a sclerosing agent.

In accordance with certain embodiments, the method further comprises inserting a guide wire into the body vessel via a central lumen of the vessel seclusion device. In such embodiments, the method further comprises inserting at least a portion of the vessel seclusion device into the body vessel via the guide wire. In further embodiments, the method further comprises positioning the vessel seclusion device with the body vessel via ultrasound. In some embodiments, the method further comprises inflating a distal balloon and a proximal balloon of the vessel seclusion device within the body vessel to define the treatment chamber. In such embodiments, inflating the distal balloon and the proximal balloon comprises separately inserting a fluid into the distal balloon via a distal balloon lumen and inserting the fluid into the proximal balloon via a proximal balloon lumen.

In yet another aspect, certain embodiments provide a method for secluding a body vessel. According to certain embodiments, the method includes selecting a seclusion length of the body vessel such that the seclusion length has a starting point and an ending point, dividing the seclusion length into at least two treatment chambers, secluding the first treatment chamber with a vessel seclusion device, moving the vessel seclusion device to the second treatment chamber, and secluding the second treatment chamber. In such embodiments, the first treatment chamber is defined by the starting point and a first intermediate point, and the second treatment chamber is defined by the first intermediate point and the ending point. In some embodiments, secluding each of the first treatment chamber and the second treatment chamber comprises removing blood from the treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port. In such embodiments, the aspiration port is operably coupled to an aspiration port lumen of a vessel seclusion device, and the injection port is operably coupled to an injection port lumen of the vessel seclusion device. According to certain embodiments, moving the vessel seclusion device comprises positioning the vessel seclusion device within the body vessel via ultrasound.

In accordance with certain embodiments, the seclusion length comprises at least three treatment chambers. In such embodiments, the first treatment chamber is defined by the starting point and the first intermediate point, the second treatment chamber is defined by the first intermediate point and a second intermediate point, and a third treatment chamber is defined by the second intermediate point and the ending point.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

What is claimed is:

1. A system for permanently closing off a vein, the system comprising:
    a sclerosing agent;
    a device for permanently closing off the vein, the device comprising:
        a lumen assembly, at least a portion of which is configured to be inserted within the vein;
        a distal balloon disposed on the lumen assembly;
        a proximal balloon disposed on the lumen assembly and spaced from the distal balloon;
        an aspiration port defined by the lumen assembly and positioned adjacent to the distal balloon;
        an injection port defined by the lumen assembly and positioned adjacent to the proximal balloon,
        wherein the lumen assembly defines a distal balloon lumen operably coupled to the distal balloon, a proximal balloon lumen operably coupled to the proximal balloon, an aspiration port lumen operably coupled to the aspiration port, and an injection port lumen operably coupled to the injection port,
        wherein within the lumen assembly the distal balloon lumen is disposed diagonally across from the proximal balloon lumen and the aspiration port lumen is disposed diagonally across from the injection port lumen,
        wherein the distal balloon and the proximal balloon are independently inflatable and deflatable,
        wherein, in an operational configuration in which the distal balloon and the proximal balloon are inflated via the distal balloon lumen and the proximal balloon lumen, respectively, the distal balloon and the proximal balloon engage the vein to define a first treatment chamber therebetween, and wherein the first treatment chamber is unobstructed by one or more balloons or visualization devices,
        wherein the aspiration port and the injection port are positioned within the first treatment chamber,
        wherein in operation the sclerosing agent is configured to enter the first treatment chamber via the injection port and the injection port lumen,
        wherein the aspiration port and the aspiration port lumen are configured to remove at least one of blood, a bodily fluid, the sclerosing agent, or any combination thereof from the first treatment chamber, and
        wherein in operation the distal balloon and the proximal balloon are configured to maintain the sclerosing agent in the first treatment chamber for a predetermined period of time such that the sclerosing agent causes the vein to collapse around the inflated distal balloon and proximal balloon such that the inflated distal balloon and proximal balloon support the vein until the distal balloon and proximal balloon are independently deflated via the distal balloon lumen and the proximal balloon lumen, respectively, such that the device can be removed from the vein, and the first treatment chamber permanently closes around the device as the device is removed from the vein.

2. The system of claim 1, wherein each of the aspiration port and the injection port comprise a port orifice and a one-way valve at the port orifice.

3. The system of claim 1, wherein each of the distal balloon and the proximal balloon are spherical.

4. The system of claim 1, wherein the distal balloon comprises a distal balloon diameter, the proximal balloon comprises a proximal balloon diameter, and each of the distal balloon diameter and the proximal balloon diameter is from about 5 mm to about 20 mm.

5. The system of claim 1, wherein the first treatment chamber comprises a length from about 3 cm to about 15 cm.

6. The system of claim 1, wherein the lumen assembly further defines a central lumen, wherein the central lumen is configured to introduce a guide wire into the vein.

7. The system of claim 1, wherein in operation the aspiration port and the aspiration port lumen are configured to remove blood or a bodily fluid and the sclerosing agent from the first treatment chamber.

8. The system of claim 1, further comprising a non-invasive external ultrasound device, the non-invasive external ultrasound device having no equipment deployed on the device for permanently closing off the vein.

9. The system of claim 8, wherein the non-invasive external ultrasound device is configured to assist positioning the device from the first treatment chamber to a second treatment chamber adjacent to the first treatment chamber within the vein.

\* \* \* \* \*